(12) United States Patent
Valaskovic et al.

(10) Patent No.: US 6,395,183 B1
(45) Date of Patent: May 28, 2002

(54) METHOD FOR PACKING CAPILLARY COLUMNS WITH PARTICULATE MATERIALS

(75) Inventors: Gary Valaskovic; Emily E. Ehrenfeld, both of Cambridge, MA (US)

(73) Assignee: New Objectives, Inc., Cambridge, MA (US)

( * ) Notice: Subject to any disclaimer, the term of this patent is extended or adjusted under 35 U.S.C. 154(b) by 0 days.

(21) Appl. No.: 09/768,895

(22) Filed: Jan. 24, 2001

(51) Int. Cl.[7] .............................................. B01D 15/08

(52) U.S. Cl. ...................... 210/656; 210/198.2; 141/12; 141/80

(58) Field of Search ............................ 210/656, 198.2, 210/635; 95/82, 88; 96/101; 141/12, 80

(56) References Cited

U.S. PATENT DOCUMENTS

| | | | |
|---|---|---|---|
| 4,483,773 A | 11/1984 | Yang | 210/656 |
| 4,793,920 A | 12/1988 | Cortes et al. | 210/198.2 |
| 4,966,696 A | 10/1990 | Allington et al. | 210/198.2 |
| H896 H | 3/1991 | Szakasits et al. | 210/198.2 |
| 5,453,163 A | 9/1995 | Yan | 204/180.1 |
| 5,679,255 A | 10/1997 | Cortes et al. | 210/656 |
| 5,997,746 A | 12/1999 | Valaskovic | 210/656 |

OTHER PUBLICATIONS

Tsuda et al., Analytical Chemistry, vol. 50, No. 2, (Feb. 1978) pp. 271–275 "Packed Microcapillary Columns in High Performance Liquid Chromatography".
Shelly et al., Analytical Chemistry, vol. 56, (1984) pp. 2990–2992 "Aids For Analytical Chemists: Dead–Volume Free Termination for Packed Columns in Microcapillary Liquid Chromatography".
Crescentini et al., Analytical Chemistry, vol. 60, (1988) pp. 1659–1662 "Preparation and Evaluation of Dry–Packed Capillary Columns for High–Performance Liquid Chromatography".
Kennedy et al., Analytical Chemistry, vol. 61, (1989) pp. 1128–1135.
Cappiello et al., Chromatographia, vol. 32, (1991) pp. 389–391 "New Materials and Packing Techniques for Micro–HPLC Packed Capillary Columns".
Fermier, et al., J. Microcolumn Separations, vol. 10, (1998) pp. 439–447 "Capillary Electrochromatography in Columns Packed by Centripetal Forces".
Li, et al., Rev. Sci. Instruments, vol. 62, (1991) pp. 2630–2633 "Polystyrene latex particles as size calibration for the atomic force microscope".
Dushkin et al., Langmuir, vol. 9, (1993) pp. 3695–3701 "Colored Multilayers from Transparent Submicrometer Spheres".

Primary Examiner—Ernest G. Therkorn
(74) Attorney, Agent, or Firm—Norris McLaughlin & Marcus

(57) ABSTRACT

Method for loading a capillary channel with a packing material to form a capillary column which comprises placing a first frit on a first capillary channel, forcing a slurry of a solid packing material in a liquid through said first channel so that the liquid, but not the solid packing material, passes through the frit and out of the capillary channel, to form a first bed of packing material within said first capillary channel and adjacent to the frit; thereby forming a pre-pack column, then removing the frit and joining the pre-pack column to an empty second capillary channel and attaching a second frit to the end of said second channel, then forcing a liquid into the end of pre-pack column, so that the liquid passes through the pre-pack column, mobilizing the packing therein and carrying it into the second capillary channel, where the liquid, but not the packing material, passes through the frit and out of said second channel, whereby said packing forms a packed bed in the second column; then separating the packed capillary column from the pre-pack column.

19 Claims, 2 Drawing Sheets

METHOD FOR PACKING CAPILLARY COLUMNS WITH PARTICULATE MATERIALS

This invention pertains to a method for preparing packed capillary columns. More particularly, the invention pertains to a multi-step method of packing capillary tubes to form packed capillary columns wherein a pre-pack column packed with particulate materials is first prepared by the slurry packing method, and then the packing is transferred from the pre-pack column to a second capillary tube to form a final packed capillary column.

BACKGROUND OF THE INVENTION

Capillary columns are capillary channels which have been packed with a packing material. Suitable channels may be fabricated from hollow tubing of appropriate diameter or formed in planer substrates through a variety of processes.

There are a variety of methods currently in use for packing capillary channels to form packed capillary columns, such as those columns used in the fields of chromatography and electrospray ionization mass spectrometry (ESI-MS).

One method for packing capillary tubes is known as the "Dry Packing Method". In accordance with this method, dry packing material, such as glass, silica, polymeric powder or metallic powder, is forced into one end of capillary tube. In a particularly advantages aspect of this method, the particulate materials are rapidly vibrated as they are loaded into the tube through a funnel.

Narrow-bore columns, which are being found useful for an expanding variety of technological applications, have inside diameters which are generally <300 $\mu$m, and typically constructed of steel, polymer or fused-silica. Especially narrow columns will be required for the so-called "lab on a chip devices" which are now in their early stages of development, in which capillary channels are fabricated in planar substrates, such as glass or silicon wafers. The "Dry Packing Method" is unsatisfactory for loading such columns, because the small diameters involved do not allow for the free flow of dry powdered material.

A second method for packing capillary tubes is known as the "Slurry Packing Method". In accordance with this method, a slurry, i.e., a liquid comprising suspended particles of packing material, is forced under pressure into the proximal end of the tube, and pumped until the slurry reaches a frit at the distal end of the tube. The frit serves to "filter" the particulate packing material from the liquid, also known as the "mobile" phase. The mobile phase thus passes through the frit and out of the tube, while the solid packing particles remain behind the frit. As the tube begins to thus become packed, the back-pressure on the system increases due to viscous flow. The packing rate, and the flow rate of the mobile phase through the tube, thus decreases as packing progresses and the amount of packing built-up behind the frit increases. In order to compensate for the increased back-pressure, and maintain a constant flow rate, the pressure of the slurry entering the tube has to be increased.

Slurry packing normally requires the use of high pressures (>1000 psi) in order to generate a high flow rate of mobile phase and resultant high "impact velocity" of the incoming particles. This high velocity forces the incoming particles into intimate contact with the bed. In this way, a tightly packed bed is formed. A tightly packed bed is important for good, reproducible chromatographic performance. This is especially important for column-to-column reproducibility. Slurry packing can be utilized to form columns in capillary channels that are frbricated in tubular or planar substrates.

The "Slurry Packing Method", while useful, generally requires the use of expensive instrumentation capable of generating and withstanding high operating pressures. This becomes much more the case as the trend towards columns having smaller and smaller inside diameters continues.

In yet a third method, the channel is filled with a monomer solution or a gel, and then the monomer is caused to polymerize inside the tube, to form a continuous porous bed through which gas or liquid may then flow. No solid material is initially introduced into the channel, and this method is based on a change in the state of the initial material charged into the channel from a liquid or gel into a porous solid.

Other known methods involve electroosmotic packing, centrifugal packing and evaporative packing.

None of the foregoing methods offer the economy and ease of use of the method we have now discovered.

SUMMARY OF THE INVENTION

We have now discovered a method for column packing based on the traditional slurry method, which is compatible with low packing pressures ($\leq$1000 psi) and narrow bore columns (<300 $\mu$m inside diameter). This method utilizes a multi-step approach that is analogous to an "annealing" or condensation process. In "annealing", residual stress or defects in a system are removed through the application of energy.

In accordance with the method, a pre-pack channel is packed with a packing material by the slurry method to form a pre-pack column. The frit is then removed from the pre-pack column, and the pre-pack column is then joined with the final channel to be packed. A fluid, such as that used as the mobile phase for the slurry packing of the pre-pack column, is then forced through the pre-pack column and into the final channel, whereby the packed material in the pre-pack column flows into the final channel to form a packed bed in the final channel, thereby forming a final packed column.

DETAILED DESCRIPTION

In accordance with the method of the present invention, a channel having a proximal end and a distal end, with a porous frit at the distal end, is first pre-packed by forcing a slurry of packing material packing into the proximal end of the channel at a slurry pressure in the range of from about 100 to about 1,000 psi. A loosely-packed bed is thereby formed in the channel, to form a pre-pack column. This loosely-packed bed, however, typically has a plurality of packing defects. Such packing defects are characterized as undesirably large void spaces within the bed. The presence of such large voids in a packed bed would cause the bed to perform poorly in chromatography service.

The frit is then removed from the distal end of the pre-pack column and the pre-pack column, or a portion thereof, is joined to the proximal end of a second channel, void of any mobile phase, having a proximal end and a distal end and having a porous frit at the distal end. The distal end of the pre-pack column is preferably secured to the proximal end of the second channel by a liquid-tight, zero dead volume, seal using a "union"; although any of the other types of devices known in the art for securing one channel to another or any other method of joining one tube to another may also be used for this purpose.

The second channel initially is empty of any liquid, although the presence of a gas, such as air, nitrogen, helium, argon or the like may be desirable. It is especially desirable to have Helium present in the second channel, as Helium is highly compressible and leads to faster travel of the slurry through the channel.

A liquid, such as the mobile phase liquid used in the slurry, is then forced through the proximal end of the pre-pack column, to force the bed of packing material out of the pre-pack column and into the second channel. As the bed flows into the second tube and flows from the proximal end of the second tube to the distal end, kinetic energy from the flowing liquid phase induces transient contact of the particles making up the bed with each other, and induces a uniform distribution of the particles within the bed. As the bed of packing material reaches the frit at the distal end of the second channel, a re-packing of the bed takes place. The re-packing takes place much more quickly than did the pre-packing, because the packing velocities of the individual particles are more uniform; that is to say, that the velocity of each individual particle will be close to the velocity of each of the other particles, so that there will be a uniform velocity profile of the particles as they move through the channel towards the frit. This has the effect of reducing the spaces between the individual particles, so that when packing takes place the amount and size of gaps between the packed particles is reduced, for a more uniform packing having less defects than has heretofore been achievable.

In a further embodiment of the invention, several pre-pack columns are stacked in succession prior to packing the "second" channel to create the packed column. This embodiment enables the preparation of longer packed columns, i.e., longer packed lengths; as well as columns having sections of different kinds of packing materials in succession.

Optionally, if further improvement in the packing is desired, the packed "second" column can then be used as a new "pre-pack" column, with a new empty "second" channel, and the process can be repeated. This can be repeated as many times as desired, until a point is reached where further processing yields diminishing degrees of improvement in the packing.

There are a variety of techniques that can be used to force the mobile phase through the distal end of the pre-pack column, and the invention is not limited to any particular method. By way of example, the slurry can be forced into the pre-pack channel by applying a gas pressure, such as air or nitrogen pressure, to the slurry itself. A vacuum can also be applied to the distal end of the pre-pack tube to "draw" the slurry in, or both a pressure on the slurry at the proximal end of the channel and a vacuum on the distal end of the channel can be used.

The packing materials used may be particles of a variety of shapes, such as spherical, hemispherical, "irregular" spheres, rods with aspect ratios of <5:1, fractured "chips" (i.e., shapes associated with finely ground materials), precipitated crystallites (tiny cubes, prisms, dodecahedral, etc.) or powders. Spherical or nearly spherical shapes are preferred, however, since such shapes allow for the most uniform and dense packing. The packing materials may be solid, hollow or porous such as, for example, solid, hollow or porous spheres.

Preferred packing materials are ceramic, metallic or polymeric. The ceramic materials which can be used include, for example, soda-lime glass, borosilicate glass, porous silica (silica gel) and non-porous silica. The metals which can be used include, for example, colloidal gold, colloidal silver, nickel and stainless steel. The polymeric materials which can be used include, for example, fluoropolymers, such as polyvinylidene fluoride (PVDF), fluorinated ethylene propylene (FEP); styrenics, such as polystyrene (PS) and polystyrene/divinylbenzene copolymer (PS/DVB); polyolefins such as high density linear polyethylene (HDPE), low-density linear polyethylene (LDPE) and polypropylene; polyketones, such as polyetheretherketone (PEEK); acrylics, such as polymethylmethacrylate (PMMA) and vinyls, such as divinylbenzene (DVB). Particularly preferred materials are borosilicate glass, silica (both porous silica and non-porous silica) and PS/DVB copolymer.

The particles which are used should have dimensions, i.e., diameters in the case of spheres, which are smaller than the smallest internal dimension of the channel to be used, if the channel has an internal shape other than round; or smaller than the internal diameter of the channel, if the channel to be used has a round internal shape; and should have maximum dimensions, or diameters if spherical, of about ½ the smallest internal dimension or diameter of the channels used. In general, the largest dimensions of non-spherical particles, or the diameters of the spherical particles used, range from about 0.1 $\mu$m to about 1 mm, although a range of 0.25 $\mu$m to about 250 $\mu$m is preferred; a range of 0.5 to 30 $\mu$m being particularly preferred, a range of 1 to 5 $\mu$m being especially preferred.

There are many liquids known to the art which can be used as a mobile phase to form the slurry. Preferred liquids are methanol, ethanol, isopropanol, methylene chloride, acetone, acetonitrile, tetrahydrdrofuran (THF) and water; although almost any liquid can be used, as long as it is not harmful to the packing material or tube. The liquid selected should thus be one that will not dissolve, swell or otherwise harm the packing material selected, although it should "wet" the surface of the packing material.

The channels which are used are those known to the art, and can, for example, be those which are generally classified as ceramics, such as borosilicate glass, fused-silica, polyimide coated fused-silica and aluminum coated fused-silica; metallic, such as stainless steel, glass lined stainless steel or silica lined stainless steel; or they can be of polymeric materials. The polymeric material which can be used include fluoropolymers, such as ethylene tetrafluoroethylene (ETFE), fluorinated ethylene propylene (FEP) and polytetrafluoroethylene(PTFE); polyolefins, such as high density linear polyethylene (HDPE), low-density linear polyethylene (LDPE) and polypropylene; polyketones, such as polyetheretherketone (PEEK) and silica-lined PEEK; acrylics, such as polymethylmethacrylate (PMMA), polyamides, such as nylon 6, nylon 11 and nylon 12; and polyimide. Preferred tubes in accordance with the invention are those of polyamide-coated fused silica, stainless steel, PEEK and HDPE, although polyimide-coated fused silica is especially preferred.

The internal or external shapes of the channels used in the practice of this invention can take on a variety of regular geometric shapes, such as round, oval, square, rectangular, polygonal, such as pentagonal, hexagonal, and the like; or can take on irregular shapes. The term "internal shape" of the channels, as used herein, has the same sense of meaning as the "bore" of a tube. Particularly preferred are those channels having a round internal shape or bore.

The channels used in the practice of the invention, having round internal shapes or bores, have inside diameters in the range of from about 1 $\mu$m to about 5 mm, preferably 10 $\mu$m to 2 mm, and particularly preferably 500 $\mu$m to 1 mm, especially tubes having inside diameters of about 75 $\mu$m to about 300 $\mu$m. Where tubes having internal shapes other than round are used, their internal cross-sectional areas should be in the same range as that of a tube having a round internal shape with a diameter in the range of from about 10 µm to about 2 mm, preferably that of a tube having a round internal shape with a diameter 50 to 250 µm and particularly preferably that of a tube having a round internal shape with a diameter 75 to 300 µm The tubes or channels can be of uniform internal dimensions or diameter over their entire length, such as those typically used for chromatography columns, or they can be tapered at one end, so that the internal diameter tapers to a narrow tip or needle, such as those columns used for electrospray ionization mass spectrometry (ESI-MS). The columns having tapered ends are also referred to in the art as needles.

The tubes or channels used for the pre-pack and second tubes can be of the same type as each other, or different. Thus, the diameter, length, cross-section, and materials of construction of one can each be independently different than that the other.

The length of the pre-pack and second columns to be used will vary with the contemplated application, as well as the amount of additional packing, if any, which is to be used in combination with the packing of the present invention. That is to say, the packing of the present invention can be used alone, or in combination with other packings which can be added to the column before or after the present packing. Packed columns with lengths of 19 meters or more are known (U.S. Pat. No. 4,793,920), and such columns can be used in the practice of this invention, for which the length of the column used is not limited.

The slurry can be prepared by conventional methods, known to those skilled in the art. One such method is simple mixing, wherein a liquid is introduced into a vessel, such as a vial, beaker or a flask, together with the packing material, and the contents are then stirred.

BRIEF DESCRIPTION OF THE DRAWINGS

As shown in FIG. 1, a slurry (60) (preferably of fused silica particles in methanol) is fed into the proximal end (1) of pre-pack tube (10). The slurry is supplied at a pressure ranging from about 100 psi to about 800 psi. Tube (10) is provided at its distal end with a removable porous frit (2). As the slurry passes through the tube and reaches the frit, the liquid or mobile phase (3) of the slurry, but not the solid particulate matter, passes through the frit and out of the tube. The particles, which are unable to pass through the frit, accumulate in front of the frit to form a pre-pack bed (4).

Figure 1:
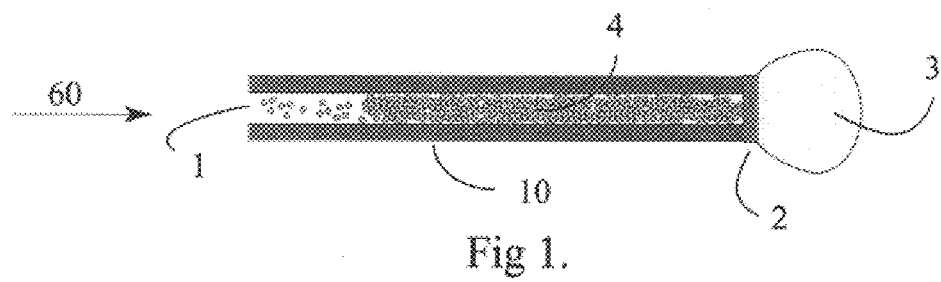
FIG. 1 is a cross sectional view of a pre-pack tube, showing slurry being forced into the tube under pressure and a packing being formed within the tube.
Figure 2:
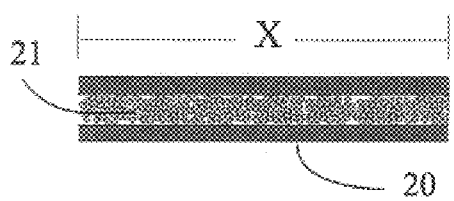
FIG. 2 is a cross sectional view of a section of the packed pre-pack column, having a loosely packed packing bed, with frit and inlet ends removed.

The removable frit is then removed from column (10), and a section of column (10) is cut out, to form pre-pack column section (20), having a length of "x", with pre-pack bed (21), as shown in FIG. 2.

Figure 3:
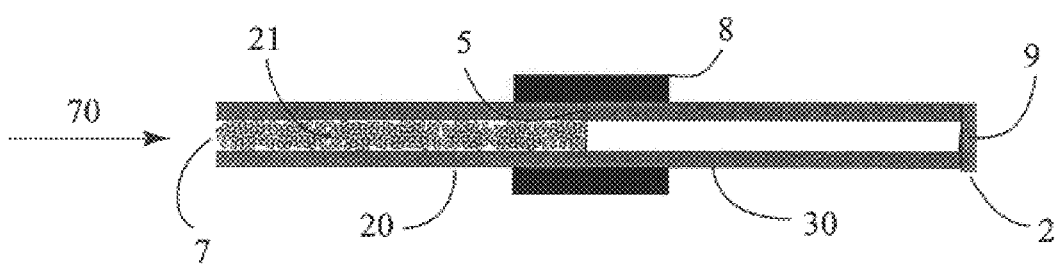
FIG. 3 is a cross sectional view of the pre-pack column section of FIG. 2 joined to a second tube, in preparation for the transfer of the packing material from the pre-pack tube section to the second tube.

Pre-pack column section (20) is then joined at one end with the proximal end of a second tube (30), and the joined ends are held together with a liquid tight seal (5) and union (8), as shown in FIG. 3. The inside of second tube (30) at the proximal end is optionally etched. Etching of the inside will slightly increase the diameter and reduce the likelihood of any clogging at the interface between the pre-pack column and second tube during subsequent passage of packing materials from one to the other, due to imperfect alignment. A frit (9), which can be the same or different type than that of the frit (2) used in preparing the pre-pack column, is placed on the distal end of second tube (30), and a liquid (70) (which is preferably the same liquid as was used as the mobile phase in the slurry(60), i.e., methanol) is forced into the open end (7) of pre-pack column (20) at a pressure of up to about 1000 psi, as shown in FIG. 3.

Figure 4:
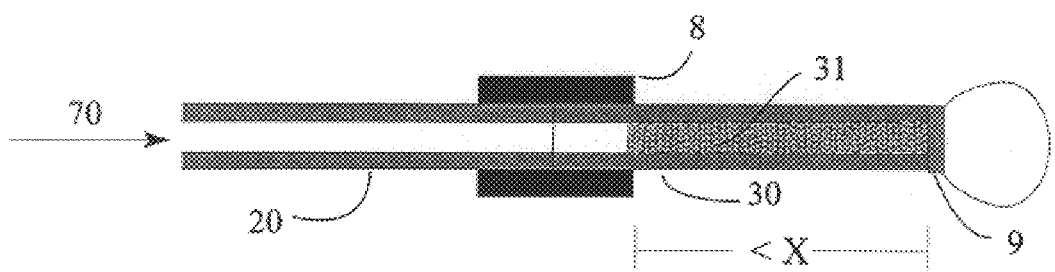
FIG. 4 is a cross sectional view of the columns of FIG. 3 after the packing has been transferred from the pre-pack column section into the second tube.

The flowing liquid induces the pre-packed bed of particles (21) in pre-pack column section (20) to become mobile once again, and to move into and through second tube (30), until frit (9) is reached. as shown in FIG. 4. The liquid passes through and out of frit (9), and the remobilized particles accumulate in front of frit (9) to form a new packed bed (31). The length (<x) of new packed bed (31) is about 15% shorter than the length of pre-packed bed (21), owing to the more efficient packing and closer packing density.

Figure 5:
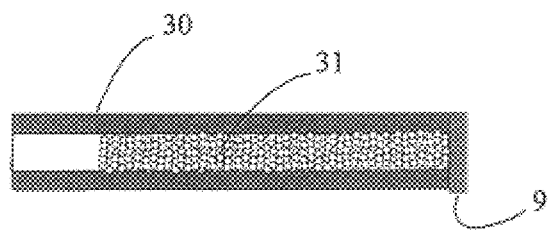
FIG. 5 is a cross sectional view of the second column after separation from the pre-pack column to form a final packed column.

The now essentially empty pre-pack column (20) is then removed from new column (30), as shown in FIG. 5.

Figure 6:
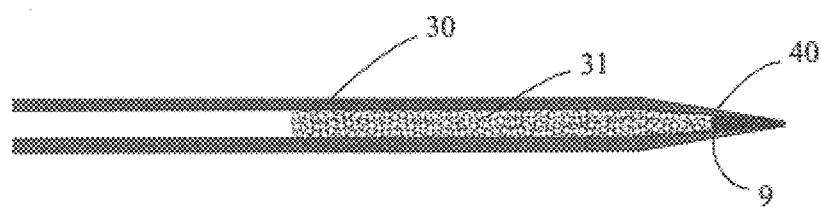
FIG. 6 is a cross sectional view of a second column having a tapered needle end suitable for use in mass spectormetry, after separation from the pre-pack column to form a final packed column.

In an alternative embodiment, the second tube (30) can be provided with a tapered needle end, to form a final column having a needle end (40) suitable for use in mass spectrometry, as shown in FIG. 6.

Figure 7:
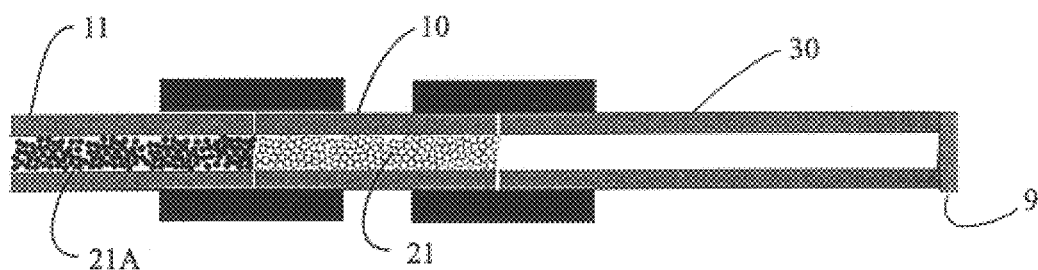
FIG. 7 is a cross sectional view showing two stacked pre-packed columns joined to a second tube, in preparation for the transfer of the packing materials from the two pre-pack columns into the second tube, to form a packed column having sections of two different packing materials.
Figure 8:
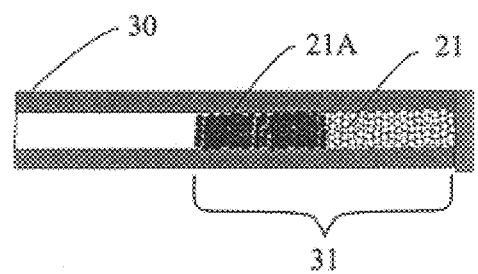
FIG. 8 is a cross sectional view showing the packed column formed by transferring the packing materials from the stacked pre-packed columns of FIG. 7 into the second tube, and separating the packed second tube from the pre-pack columns to form the final packed column.

Packed columns having a two or more different kinds of packings (21, 21A) arranged in succession, such as is shown in FIG. 8, can also be advantageously prepared in accordance with the present method. In preparing such packed columns, two or more pre-pack columns (10, 11) may be prepared, using at least two different kinds or types of packing materials (21, 21A). The pre-pack columns are then joined together in series, as shown in FIG. 7, and a second tube (30) is then joined to the remaining open end of one of the two joined pre-pack columns, in the same manner as described above. A frit (9) is placed on the distal end of the second column, in the same manner as described above, and a liquid is then forced into the remaining open end of the joined pre-pack columns in the same manner as described above, to mobilize the packings in both pre-pack columns and repack them into the second tube in the same manner as described above; after which the packed second tube is separated from the pre-pack columns, to form the packed column of FIG. 8.

As shown in FIG. 7, a first pre-pack column (10) is joined to a second pre-pack column (11). Pre-pack column (10) is packed with packing (21) and pre-pack column (11) is packed with packing (21A). Packing (21) is a different species of packing than packing (21A). Second tube (30) is joined to the distal end of pre-pack column (10) and a frit (9) is attached to the distal end of empty tube (30). A liquid (not shown) is then forced into the proximal end of pre-pack column (11), which liquid then flows through pre-pack column (11), into and through pre-pack column (10) and then into and through second tube (30). Packing (21A) and packing (21) are mobilized by the flow of liquid through the pre-pack columns, and are carried by the flowing liquid into and second column (30) where they are formed into a packed section (31) comprising a serial arrangement of packings (21A) and (21).

EXAMPLE

A slurry of 5 $\mu$m diameter C18 derivitized silica in methanol (0.02 $\mu$m of silica dispersed in 1 gm of methanol) was forced at a pressure of 800 psi, using a "pressure bomb" into a 30 cm length of 75 $\mu$m fused silica tubing, having a removable PEEK frit at its proximal end. The total packing time was 10 minutes. The frit was then removed, and a 11.8 cm. packed section was cut out of the middle of the 30 cm length of tubing. The 11.8 cm section ("pre-packed section") remained intact during the cutting, and the integrity of the bed within the section was verified with light microscopy.

The 11.8 cm length of pre-pack tubing was connected at its distal end to the proximal end of a second piece of 75 $\mu$m ID fused-silica which was 45 cm in length, having a frit attached to its distal end. The connection of the tubes to each other was made with a liquid tight, zero dead volume, union made of PEEK. The proximal end of the pre-pack section was connected to a pressure bomb which contained only methanol. The menthol was then charged into the pre-pack column. Remobilization of the packing material and repacking in the second tube took place in <5 seconds. Greater than 95% of the second column packed in less than 2 seconds.

The length of the new packed section in the second column was 10 cm. The significant reduction in packed bed length (15%) and in packing time (98%) indicate a more efficient packing of the material. The 15% reduction in length of the packed bed could not be attributed to any significant loss in packing material during the transfer process.

Additional experiments resulted in packed bed length reductions of from 5% to 20%.

The present method of packing columns is useful for a wide variety of columns, packings and conditions. Conventional LC columns, having diameters of, for example, 1 to 4.6 mm ID, could be used, as could micro-bore columns having inside diameters as small as 0.5 to 1.0 mm. The present method is especially useful for the packing of nanobore columns, having diameters of ≦300 $\mu$m or even <100 $\mu$m with small diameter packing materials (i.e., <10 $\mu$m, preferably <7 $\mu$m and most preferably in the range of 1.5 to 5 $\mu$m.

The invention and its advantages are readily understood from the foregoing description. It is apparent that various changes can be made in the process without departing from the spirit and scope of the invention. The process as herein presented, is merely illustrative of preferred embodiments of the invention, and not a limitation thereof.

We claim:

1. A method for loading a capillary channel with a packing material to form a capillary column, which comprises placing a first frit on a first capillary channel, said first capillary channel having a proximal end and a distal end and said first frit being placed on the distal end; forcing a slurry of a solid packing material in a liquid into the proximal end of said first channel so that the slurry passes from the proximal end to the distal end at which end the liquid, but not the solid packing material, passes through said first frit and out of said first capillary channel, to form a first bed of packing material within said first capillary channel and adjacent to said first frit; thereby forming a pre-pack column, then removing said first frit and joining the distal end of said pre-pack column to the proximal end of an empty second capillary channel, said second capillary channel having a proximal end and a distal end, and attaching a second frit to the distal end of said second channel, said second frit being the same as or different than said first frit, then forcing a liquid into the proximal end of said pre-pack column, so that the liquid passes through the pre-pack column, mobilizing the packing in said first bed and carrying said packing into said second capillary channel and to the distal end thereof, where the liquid, but not said packing material, passes through said second frit and out of said second channel and said packing forms a second bed adjacent to said second frit to form a packed capillary column; then separating said packed capillary column from said pre-pack column.

2. The method of claim 1, wherein said distal end of said pre-pack column is joined to the proximal end of said second capillary channel with a liquid tight, zero dead volume, union.

3. The method of claim 1, wherein said liquid is a member of the group consisting of methanol, ethanol, isopropanyl, methylene chloride, acetone, acetonitrile, tetrahydrdrofuran and water.

4. The method of claim 1, wherein said packing material is selected from the group consisting of soda-lime glass, borosilicate glass, porous silica, non-porous silica, colloidal gold, colloidal silver, nickel, stainless steel, polyvinylidene fluoride, fluorinated ethylene propylene, polystyrene, polystyrene/divinylbenzene copolymer, high density linear polyethylene, low-density linear polyethylene, polypropylene, polyetheretherketone, polymethylmethacrylate and divinylbenzene.

5. The method of claim 1 wherein each of said columns independently of the other has an inside diameter of from about 1 $\mu$m to about 5 mm.

6. The method of claim 1 wherein each of said columns independently of the other has an inside diameter of from about 10 $\mu$m to about 2 mm.

7. The method of claim 1 wherein each of said columns independently of the other has an inside diameter of from about 50 $\mu$m to about 1 mm.

8. The method of claim 1 wherein each of said columns independently of the other has an inside diameter of from about 75 $\mu$m to about 300 $\mu$m.

9. The method of claim 1 wherein each of said channels are of oval, square, rectangular, polygonal or irregular shape, and have internal cross-sections equal to that of a round-shaped channel having a diameter of from about 1 $\mu$m to about 5 mm.

10. The method of claim 1 wherein each of said channels are of oval, square, rectangular, polygonal or irregular shape, and have internal cross-sections equal to that of a round-shaped channel having a diameter of from about 10 $\mu$m to about 2 mm.

11. The method of claim 1 wherein each of said channels are of oval, square, rectangular, polygonal or irregular shape, and have internal cross-sections equal to that of a round-shaped channel having a diameter of from about 75 $\mu$m to about 300 $\mu$m.

12. The method of claim 1 wherein the inside of said second channel at the distal end is etched.

13. The method of claim 1, wherein said channels, independent of each other, are of borosilicate glass, fused-silica, polyimide coated fused-silica, aluminum coated fused-silica, stainless steel, glass lined stainless steel, silica lined stainless steel, ethylene tetrafluoroethylene, fluorinated ethylene propylene, polytetrafluoroethylene, high density linear polyethylene), low-density linear polyethylene, polypropylene, polyetheretherketone silica-lined polyetheretherketone, polymethylmethacrylate, nylon 6, nylon 11, nylon 12 or polyamide.

14. The method of claim 1 wherein said channels are capillary channels fabricated in planer substrates.

15. The method of claim 1 wherein said slurry is forced into said first channel by applying a pressure to said slurry.

16. The method of claim 1 wherein said slurry is forced into one end of said first channel by applying a vacuum to the other end of said first channel and drawing said slurry into said column.

17. The method of claim 1, wherein a plurality of pre-pack columns are prepared and joined to each other to form a combination pre-pack column having a proximal end and a distal end, and said combination pre-pack column is used as the pre-pack column.

18. The method of claim 17, wherein at least one of said plurality of pre-pack columns is packed with a different packing material than at least one other of said plurality of said pre-pack columns.

19. The method of claim 1, wherein a packed column prepared according to said method is substituted for said pre-pack column and used to prepare a second packed column.

* * * * *

UNITED STATES PATENT AND TRADEMARK OFFICE
CERTIFICATE OF CORRECTION

PATENT NO.     : 6,395,183 B1
DATED          : May 28, 2002
INVENTOR(S)    : Gary Valscovic and Emily A. Ehrenfeld It is certified that error appears in the above-identified patent and that said Letters Patent is hereby corrected as shown below:

<u>Title page,</u>
Item [75], Inventors, change the middle initial of the second inventor from:
"E" to -- A --
Item [73], Assignee, change "New Objectives, Inc" to -- New Objective, Inc. --

Signed and Sealed this

Eleventh Day of February, 2003

JAMES E. ROGAN
*Director of the United States Patent and Trademark Office*